(12) United States Patent
Hagiya

(10) Patent No.: US 7,939,697 B2
(45) Date of Patent: May 10, 2011

(54) FLUORINATING AGENT AND METHOD FOR PRODUCING FLUORINE-CONTAINING COMPOUND USING THE SAME

(75) Inventor: Koji Hagiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 97 days.

(21) Appl. No.: 12/458,820

(22) Filed: Jul. 23, 2009

(65) Prior Publication Data

US 2009/0287025 A1    Nov. 19, 2009

Related U.S. Application Data

(62) Division of application No. 10/583,608, filed as application No. PCT/JP2004/019671 on Dec. 21, 2004, now Pat. No. 7,569,703.

(30) Foreign Application Priority Data

| Dec. 25, 2003 | (JP) | .................. | 2003-429133 |
| Dec. 25, 2003 | (JP) | .................. | 2003-429134 |
| Mar. 11, 2004 | (JP) | .................. | 2004-068703 |
| Jun. 21, 2004 | (JP) | .................. | 2004-182102 |

(51) Int. Cl.
*C07C 22/00* (2006.01)

(52) U.S. Cl. ..................................... 570/127

(58) Field of Classification Search .................. 570/127
See application file for complete search history.

(56) References Cited

U.S. PATENT DOCUMENTS

| 4,780,559 A | 10/1988 | Brown et al. |
| 6,881,698 B2 | 4/2005 | Bonnet et al. |
| 2004/0144947 A1 | 7/2004 | Garayt et al. |

FOREIGN PATENT DOCUMENTS

| JP | 4-124146 | 4/1992 |
| JP | 2002-348266 | 12/2002 |
| JP | 2003-335734 | 11/2003 |
| WO | WO 03/076366 A2 | 9/2003 |

OTHER PUBLICATIONS

Badone et al., "Use of Polyethylene Glycol in the Synthesis of Alkyl Fluorides from Alkyl Sulfonates", Synthesis, 1987, pp. 920-921.
Bosch et al., "Tetrabutylammonium Bifluoride: A Versatile and Efficient Fluorinating Agent", Tetrahedron Letters, 1987, vol. 28, No. 40, pp. 4733-4736.
Bram et al., "Easy and Efficient Heterogeneous Nucleophilic Fluorination without Solvent", Synthetic Communications, 1988, vol. 18, No. 14, pp. 1661-1667.
Clark et al., "Calcium Fluoride-supported Alkali Metal Fluorides. New Reagents for Nucleophilic Fluorine Transfer Reactions", J. Chem. Soc., Chem. Commun., 1986, pp. 791-793.
Cox et al., "Anhydrous Tetrabutylammonium Fluoride: A Mild but Highly Efficient Source of Nucleophilic Fluoride Ion", J. Org. Chem, 1984, vol. 49, pp. 3216-3219.

Cuomo et al., "An Efficient and Convenient Synthesis of Fluroformates and Carbamoyl Fluorides", J. Org. Chem., 1979, vol. 44, No. 6, pp. 1016-1017.
Dermeik et al, "Effect of Water on the Extraction and Reactions of Fluoride Anion by Quaternary Ammonium Phase—Transfer Catalysts", J. Org. Chem., 1985, vol. 50, pp. 879-882.
Finger et al., Aromatic Fluorine Compounds. VII. Replacement or Aromatic—Cl and—$NO_2$ Groups by—$F^{1,2}$, J. Am. Chem. Soc., 1956, vol. 78, pp. 6034-6039.
Hagiwara et al., "Acidic 1-ethyl-3-methylimidazolium fluoride: a new room temperature ionic liquid", Journal of Fluorine Chemistry, vol. 99, 1999, pp. 1-3.
Ichihara et al., "The Combination of Potassium Fluoride and Calcium Fluoride: A Useful Heterogeneous Fluorinating Reagent", Chem. Commun., 1986, pp. 793-794.
Ishikawa et al., "Enhanced Effect of Spray-Dried Potassium Fluoride on Fluorination", Chemistry Letters, 1981, pp. 761-764.
Sekiya et al., "Preparation of Aroyl and Arenesulfonyl Fluorides from the Corresponding Chlorides Using Zinc Fluoride-Pyridine System", 1978, Bulletin of the Chemical Society of Japan, vol. 51, No. 4, pp. 1267-1268.
Swatloski et al., "Ionic liquids are not always green: hydrolysis of 1-butyl-3-methylimidazolium hexafluorophosphate", Green Chemistry, 2003, vol. 5, pp. 361-363.
Hagiwara et al., 2003, CAS:140:70401.
Urahata et al., 2004, CAS: 140:303126.
Hirano et al., 1995, CAS: 123:2847a.

(Continued)

*Primary Examiner* — Rei-tsang Shiao
(74) *Attorney, Agent, or Firm* — Foley & Lardner LLP

(57) ABSTRACT

A method for producing a fluorine-containing organic compound represented by the formula (7):

R—Fm     (7)

wherein R represents a substituted or unsubstituted saturated hydrocarbon group, or a substituted or unsubstituted aromatic group and m represents an integer satisfying the inequality: $1 \leq m \leq n$,
which comprises reacting a fluorinating agent represented by the formula (1):

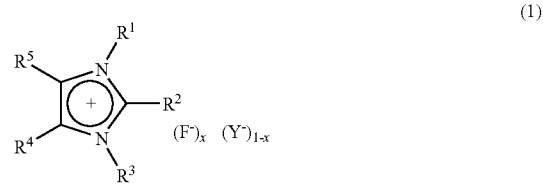

(1)

wherein $R^1$ and $R^3$ are the same or different, and represent an optionally substituted alkyl group, $R^2$, $R^4$ and $R^5$ are the same or different, and represent a hydrogen atom or an optionally substituted alkyl group, x satisfies $0<x \leq 1$, and $Y^-$ represents a monovalent anion other than a fluoride ion,
with an organic compound of the formula (6):

R-Ln     (6)

wherein R is the same as defined above, L represents a leaving group and n represents an integer of 1 or more, and a fluorinating agent using the same are described.

11 Claims, No Drawings

OTHER PUBLICATIONS

Miyauchi et al., 2003, CAS: 139:395934.

Hagiwara et al., 2002, CAS: 138:45060.

Mori et al., 1991, CAS: 114:216779.

Ue et al., "Ionic Liquids with Low Melting Points and Their Application to Double-Layer Capacitor Electrolytes", Electrochemical and Solid-State Letters, 2002, vol. 5, No. 6, pp. A119-A121.

FLUORINATING AGENT AND METHOD FOR PRODUCING FLUORINE-CONTAINING COMPOUND USING THE SAME

This application is a divisional application of U.S. application Ser. No. 10/583,608, filed Jun. 20, 2006, which is the National Stage application of International Application No. PCT/JP04/19671, filed Dec. 21, 2004, which claims the priority to Japan Application Nos. 2003-429133 and 2003-429134, both filed Dec. 25, 2003, and Japan Application No. 2004/068703, filed Mar. 11, 2004, and Japan Application No. 2004/182102, filed Jun. 21, 2004. All of which are hereby incorporated by reference in their entirety.

BACKGROUND OF THE INVENTION

1. Technical Field

The present invention relates to a method for producing a fluorine-containing compound, which is an important as various chemical products such as pharmaceutical and pesticide compounds and electronic materials and the intermediates thereof, and a fluorinating agent.

2. Background Art

Methods for substituting a halogen atom or a sulfonyloxy group to a fluorine atom by reacting a compound subjected to the nucleophilic substitution reaction such as a halogenated compound or a sulfonate with potassium fluoride as a fluorinating agent have been known (e.g. patent document 1, patent document 2, non-patent document 1, non-patent document 2 and non-patent document 3).

A method for using a quaternary ammonium fluoride as a fluorinating agent (e.g. non-patent document 4) and a method for using a quaternary ammonium fluoride in combination with cesium fluoride (e.g. non-patent document 5) have been known. Further, methods for using a quaternary ammonium bifluoride or a quaternary phosphonium bifluoride, which contains hydrogen fluoride and is synthesized using a highly corrosive and toxic hydrofluoric acid, have been known (e.g. non-patent document 6, patent documents 3 and 4).

Patent document 1: WO02/092608
Patent document 2: WO03/076366
Patent document 3: JP 61-161224 A
Patent document 4: JP 4-124146 A
Non-patent document 1: J. Amer. Chem. Soc., 78, 6034 (1956)
Non-patent document 2: Chemistry Lett., 761 (1981)
Non-patent document 3: Synthesis, 920 (1987)
Non-patent document 4: J. Org. Chem., 49, 3216 (1984)
Non-patent document 5: Synthetic Commun., 18, 1661 (1988)
Non-patent document 6: Tetrahedron Lett., 28, 4733 (1987)

It has been known that 1-ethyl-3-methylimidazolium fluoride as an electrolyte raw material is obtained by reacting a methanol solution of the corresponding imidazolium carbonate with ammonium fluoride or with potassium fluoride in water solvent (e.g. non-patent document 8 and patent document 5). Further, a method for obtaining 1-ethyl-3-methylimidazolium fluoride as the hydrogen fluoride adduct by reacting 1-ethyl-3-methylimidazolium chloride with hydrogen fluoride has been known (e.g. non-patent document 7). It has been known that 1-butyl-3-methylimidazolium fluoride hydrate is produced by pyrolyzing 1-butyl-3-methylimidazolium fluoride hexafluorophosphate (e.g. non-patent document 9).

Patent document 5: JP 2003-335734 A
Non-patent document 7: J. Fluorine. Chem., 99, 1 (1999)
Non-patent document 8: Electrochemical and Solid-State Letters, 5(6) A119-A121 (2002)
Non-patent document 9: Green Chemistry, 2003, 5, 361-363

DISCLOSURE OF THE INVENTION

According to the present invention, a fluorine-containing compound can be readily produced.

The first embodiment of the present invention is a method for producing a fluorine-containing organic compound represented by the formula (7):

wherein R represents a substituted or unsubstituted saturated hydrocarbon group, or a substituted or unsubstituted aromatic group and m represents an integer satisfying the inequality: $1 \leq m \leq n$,
which comprises reacting an imidazolium salt represented by the formula (1):

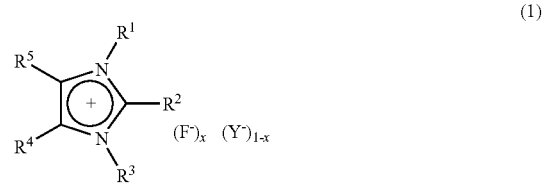

wherein $R^1$ and $R^3$ are the same or different, and represent an optionally substituted alkyl group,
$R^2$, $R^4$ and $R^5$ are the same or different, and represent a hydrogen atom or an optionally substituted alkyl group, x satisfies $0<x\leq1$, and
$Y^-$ represents a monovalent anion other than a fluoride ion, with an organic compound of the formula (6):

wherein R is the same as defined above, L represents a leaving group and n represents an integer of 1 or more.

The second embodiment of the present invention relates to an imidazolium salt anhydride represented by the formula (1):

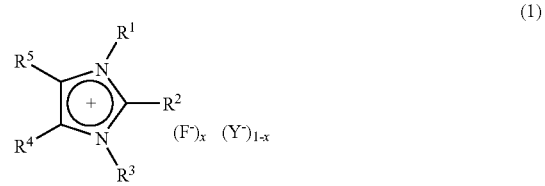

wherein $R^1$ and $R^3$ are the same or different, and represent an optionally substituted alkyl group,
$R^2$, $R^4$ and $R^5$ are the same or different, and represent a hydrogen atom or an optionally substituted alkyl group, x satisfies $0<x\leq1$, and
$Y^-$ represents a monovalent anion other than a fluoride ion,
provided that excepting in a case that when x represents 1, either $R^1$ or $R^3$ represents a methyl group and the other represents an ethyl group.

The third embodiment of the present invention relates to an imidazolium salt of the formula (1):

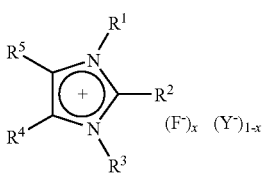

(1)

wherein $R^1$ and $R^3$ are the same or different, and represent an optionally substituted alkyl group, $R^2$, $R^4$ and $R^5$ are the same or different, and represent a hydrogen atom or an optionally substituted alkyl group, x satisfies 0<x<1, and $Y^-$ represents a monovalent anion other than a fluoride ion.

The fourth embodiment of the present invention relates to a method for producing an imidazolium salt represented by the formula (3):

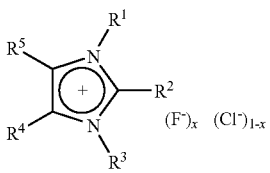

(3)

wherein $R^1$ and $R^3$ are the same or different, and represent an optionally substituted alkyl group, $R^2$, $R^4$ and $R^5$ are the same or different, and represent a hydrogen atom or an optionally substituted alkyl group, and x satisfies 0<x≦1, which comprises reacting an alkyl-substituted imidazolium chloride represented by the formula (2):

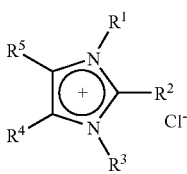

(2)

wherein $R^1$, $R^2$, $R^3$, $R^4$ and $R^5$ are as defined above, with a silver fluoride.

The fifth embodiment of the present invention relates to a method for producing an alkyl-substituted imidazolium salt containing a fluoride ion represented by the formula (5):

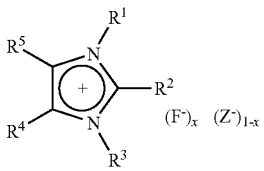

(5)

wherein $R^1$ and $R^3$ are the same or different, and represent an optionally substituted alkyl group, $R^2$, $R^4$ and $R^5$ are the same or different, and represent a hydrogen atom or an optionally substituted alkyl group, $Z^-$ represents a chloride ion or a bromide ion and x satisfies 0<x≦1, which comprises reacting an imidazolium salt represented by the formula (4):

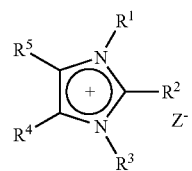

(4)

wherein $R^1$, $R^2$, $R^3$, $R^4$, $R^5$ and $Z^-$ are as defined above, with potassium fluoride in methanol.

BEST MODE FOR CARRYING OUT THE PRESENT INVENTION

First, an alkyl-substituted imidazolium salt containing a fluoride ion represented by the formula (1) (hereinafter, simply referred to as the fluorinating agent (1)) will be illustrated.

Examples of the alkyl group represented by $R^1$, $R^2$, $R^3$, $R^4$ and $R^5$ include a straight chain, branched chain or cyclic C1-20 alkyl group such as a methyl, ethyl, n-propyl, isopropyl, n-butyl, isobutyl, sec-butyl, tert-butyl, n-pentyl, hexyl, heptyl, octyl, nonyl, n-decyl, undecyl, dodecyl, tridecyl, tetradecyl, pentadecyl, hexadecyl, heptadecyl, octadecyl, nonadecyl, icosyl, cyclopropyl, 2,2-dimethylcyclopropyl, cyclopentyl, cyclohexyl and menthyl group.

The alkyl group may be substituted with at least one substituent selected from substituent groups of A to I described below.

A: C1-20 alkoxy groups and fluorine-substituted C1-20 alkoxy groups (for example, a methoxy, ethoxy, n-propoxy, isopropoxy, n-butoxy, isobutoxy, sec-butoxy, tert-butoxy and trifluoromethoxy group)

B: C6-20 aryl groups (for example, a phenyl group) and C6-20 aryl groups substituted with an alkyl group (for example, a C1-3 alkyl group) and/or an alkoxy group (for example, a C1-3 alkoxy group) (specifically, a 4-methylphenyl and 4-methoxyphenyl group)

C: C6-20 aryloxy groups (for example, a phenoxy group) and C6-20 aryloxy groups substituted with an alkyl group (for example, a C1-3 alkyl group) and/or an alkoxy group (for example, a C1-3 alkoxy group) (for example, a 2-methylphenoxy, 4-methylphenoxy, 4-methoxyphenoxy and 3-phenoxyphenoxy group)

D: C7-20 aralkyloxy groups and C7-20 aralkyloxy groups substituted with an alkyl group (for example, a C1-3 alkyl group) and/or an alkoxy group (for example, a C1-3 alkoxy group) (for example, a benzyloxy, 4-methylbenzyloxy, 4-methoxybenzyloxy and 3-phenoxybenzyloxy group)

E: a fluorine atom

F: C2-20 alkylcarbonyl groups (for example, an acetyl and ethylcarbonyl group)

G: C7-20 arylcarbonyl groups (for example, a benzoyl group) and C7-20 arylcarbonyl groups substituted with an alkyl group (for example, a C1-3 alkyl group) and/or an alkoxy group (for example, a C1-3 alkoxy group) (for example, a benzoyl, 2-methylbenzoyl, 4-methylbenzoyl and 4-methoxybenzoyl group)

H: C8-20 aralkylcarbonyl groups (for example, a benzylcarbonyl group) and C8-20 aralkylcarbonyl groups substituted with an alkyl group (for example, a C1-3 alkyl group)

and/or an alkoxy group (for example, a C1-3 alkoxy group) (for example, 4-methylbenzylcarbonyl and 4-methoxybenzylcarbonyl group)

I: a carboxyl group

Examples of the substituted alkyl group include a fluoromethyl, trifluoromethyl, methoxymethyl, ethoxymethyl, methoxyethyl, benzyl, 4-fluorobenzyl, 4-methylbenzyl, phenoxymethyl, 2-oxopropyl, 2-oxobutyl, phenacyl and 2-carboxyethyl group.

When x satisfies $0<x<1$, examples of $Y^-$ include a halide ion other than a fluoride ion such as a chloride ion, a bromide ion and an iodide ion; a borate ion such as a tetrafluoroborate anion; a phosphate ion such as a hexafluorophosphate anion; an antimonate ion such as a hexafluoroantimonate anion; a sulfonate ion such as a trifluoromethanesulfonate anion; a nitrate ion; a carbonate ion such as a carbonate ion and a methylcarbonate ion; a carboxylate ion such as an acetate ion and a trifluoroacetate ion; and an amide ion such as a bis(trifluoromethylsulfonyl)amide anion.

X can be selected at random in the range of $0<x\leq1$. When x is close to 0, the fluorination efficiency goes down and when x is close to 1, the melting point tends to become high. Therefore, x preferably satisfies a range of about $0.4<x<0.9$ in order to conduct fluorination efficiently at lower temperature.

When x is 1, examples of the fluorinating agent (1) include an alkyl-substituted imidazolium fluoride such as 1,3-dimethylimidazolium fluoride, 1,2,3-trimethylimidazolium fluoride, 1,2,3,4-tetramethylimidazolium fluoride, 1,2,3,4,5-pentamethylimidazolium fluoride, 1-methyl-3-ethylimidazolium fluoride, 1,2-dimethyl-3-ethylimidazolium fluoride, 1,3-diethylimidazolium fluoride, 1-methyl-3-(n-propyl)imidazolium fluoride, 1-methyl-3-(n-butyl)imidazolium fluoride, 1,2-dimethyl-3-(n-butyl)imidazolium fluoride, 1-methyl-3-(n-pentyl)imidazolium fluoride, 1-methyl-3-(n-hexyl)imidazolium fluoride, 1-methyl-3-(n-octyl)imidazolium fluoride, 1,3-dimethyl-2-ethylimidazolium fluoride, 1,3-dimethyl-2-(n-propyl)imidazolium fluoride, 1,3-dimethyl-2-(n-butyl)imidazolium fluoride, 1-dodecyl-2-methyl-3-dodecylimidazolium fluoride, 1-dodecyl-2-methyl-3-benzylimidazolium fluoride, 1-ethoxymethyl-3-methylimidazolium fluoride, 1-methyl-3-(methoxyethoxymethyl)imidazolium fluoride and 1-trifluoromethyl-3-methylimidazolium fluoride.

When x satisfies $0<x<1$ in the formula (1), specific examples of the imidazolium salt include an imidazolium salt consisting of an imidazolium cation such as 1,3-dimethylimidazolium cation, 1,2,3-trimethylimidazolium cation, 1,2,3,4-tetramethylimidazolium cation, 1,2,3,4,5-pentamethylimidazolium cation, 1-methyl-3-ethylimidazolium cation, 1,2-dimethyl-3-ethylimidazolium cation, 1,3-diethylimidazolium cation, 1-methyl-3-(n-propyl)imidazolium cation, 1-methyl-3-(n-butyl)imidazolium cation, 1,2-dimethyl-3-(n-butyl)imidazolium cation, 1-methyl-3-(n-pentyl)imidazolium cation, 1-methyl-3-(n-hexyl)imidazolium cation, 1-methyl-3-(n-octyl)imidazolium fluoride, 1,3-dimethyl-2-ethylimidazolium cation, 1,3-dimethyl-2-(n-propyl)imidazolium cation, 1,3-dimethyl-2-(n-butyl)imidazolium cation, 1-dodecyl-2-methyl-3-dodecylimidazolium cation, 1-ethoxymethyl-3-methylimidazolium cation, 1-methyl-3-(methoxyethoxymethyl)imidazolium fluoride, 1-trifluoromethyl-3-methylimidazolium cation and 1-(n-dodecyl)-2-methyl-3-benzylimidazolium cation, and both of a fluoride ion and a chloride ion. Further, those imidazolium salts in which the chloride ions of the above-mentioned imidazolium salts are replaced with bromide ions, iodide ions, tetrafluoroborate anions, hexafluorophosphate anions, hexafluoroantimonate anions, trifluoromethanesulfonate anions, nitrate anions, carbonate anions, acetate anions or bis(trifluoromethylsulfonyl)amide anions are exemplified.

Unless otherwise stated, the imidazolium salt (1) of the fluorinating agent of the present invention includes a salt anhydrate or that which forms a complex with a compound which is inactive to a nucleophilic substitution fluorination reaction such as water, a polar solvent or both.

The fluorinating agent (1) can be produced using a method such as salt-exchange reaction of a fluoride such as a silver fluoride and potassium fluoride and the imidazolium salt wherein x satisfies $0\leq x<1$ in the formula (1). The salt wherein x is any value may be prepared by mixing the imidazolium salt wherein x satisfies $0\leq x<1$ in the formula (1) and the imidazolium fluoride wherein x is 1.

The imidazolium chloride (1) can be produced, for example, according to a known method such as a reaction of a substituted imidazole compound and an alkyl chloride (e.g. Tetrahedron, 59, 2253 (2003)).

The method for producing the imidazolium salt fluoride by salt-exchange reaction using a silver fluoride and potassium fluoride will be illustrated in detail below.

First, the method for producing the imidazolium salt containing a chloride anion and a fluoride anion of the formula (3) (hereinafter, simply referred to as the imidazolium salt (3)) by contacting the imidazolium chloride of the formula (2) with the silver fluoride will be illustrated.

The silver fluoride has a monovalent and divalent one, and both can be used. The monovalent silver fluoride is preferably used. As the monovalent silver fluorides, two kinds thereof, silver(I) fluoride and silver subfluoride, are exemplified. Silver(I) fluoride is more preferably used from the point of cost.

The amount of the silver fluoride to be used is accordingly adjusted to make x become the desirable value in a range of $0<x\leq1$ in the formula (3) and is used. For example, when the imidazolium fluoride wherein x is 1 as the imidazolium salt (3) is desired, the purpose can be accomplished by using 1 mole or more of the silver fluoride relative to 1 mole of the imidazolium chloride (2). It is usually a range of 1 to 2 moles, preferably a range of about 1.0 to 1.1 moles.

The present reaction is usually carried out in the presence of an organic solvent, water or a mixture thereof and may be carried out without using the solvent.

Examples of the organic solvent include an ether solvent such as methyl tert-butyl ether and tetrahydrofuran; a nitrile solvent such as acetonitrile and propionitrile; an amide solvent such as dimethylformamide and dimethylacetamide; and a sulfur-containing solvent such as sulfolane and dimethylsulfoxide.

The amount of the solvent to be used is not particularly limited and in consideration of volumetric efficiency, it is usually about 100 parts by weight or less relative to 1 part by weight of the alkyl-substituted imidazolium chloride (2).

The reaction temperature is usually a range of about −20 to 200° C.

The mixing order of the reaction agents is not particularly limited. For example, the silver fluoride may be added into the solution containing the imidazolium chloride (2) under the condition of the reaction temperature and they may be added in the inverted order. After both agents and the solvent are simultaneously mixed, the reaction temperature may be adjusted.

The present reaction may be carried out under an ordinary pressure condition or a pressurized condition.

After completion of the reaction, silver chloride formed in the ion-exchange is usually precipitated in the system. After removing this using a conventional method such as filtration and decantation, the alkyl-substituted imidazolium salt (3) containing a fluoride ion can be isolated by concentrating the obtained solution. The alkyl-substituted imidazolium salt (3) containing a fluoride ion isolated may be further purified by a means such as crystallization and column chromatography.

The ending point of the reaction may be confirmed by a conventional analytical method such as ion chromatography and when silver chloride is precipitated, the reaction may be finished at the point of confirming that the precipitate does not increase.

The imidazolium salt (5) can be also obtained by contacting the imidazolium salt (4) and potassium fluoride in methanol.

A commercially available potassium fluoride can be used as it is. The amount thereof to be used is not particularly limited and the purpose of the present invention is usually accomplished by using about 0.4 to 2 moles thereof relative to 1 mole of the imidazolium salt (4).

A little amount of water or the other organic solvent may be contained in methanol used in the present invention and that in which methanol content is about 90% or more is usually used. The amount thereof to be used is not particularly limited and it is usually about 100 parts by weight or less relative to 1 part by weight of the imidazolium salt (4).

The reaction temperature is usually a range of about −20 to 200° C.

X in the imidazolium salt (5) is a value in a range of $0<x\leq1$. Depending on the desired value of x, the amount of potassium fluoride and methanol to be used, water content and the reaction temperature may be accordingly decided chiefly and the reaction may be carried out.

The mixing order of the reaction agents is not particularly limited and for example, potassium fluoride may be added into the solution containing the imidazolium salt (4) under the condition of the reaction temperature and they may be added in the inverted order. After both agents and the solvent are simultaneously mixed, the reaction temperature may be adjusted.

The present reaction may be carried out under an ordinary pressure condition or a pressurized condition. The progress of the reaction can be confirmed by a conventional analytical means such as ion chromatography, NMR and IR.

After completion of the reaction, potassium chloride or potassium bromide formed in the ion-exchange is usually precipitated in the system. After removing this using a conventional method such as filtration and decantation, the alkyl-substituted imidazolium salt (5) can be obtained by concentrating the obtained solution. When potassium chloride or potassium bromide, and potassium fluoride remained are precipitated in process of the concentration, the concentration may be carried out again after removing these inorganic salts by the above-mentioned conventional method. The imidazolium salt (5) obtained may be further purified, if necessary, by a means such as crystallization and column chromatography.

The method for producing a fluorine-containing organic compound represented by the formula (7):

$$R—F_m \quad (7)$$

wherein R represents a substituted or unsubstituted saturated hydrocarbon group, or a substituted or unsubstituted aromatic group and m represents an integer satisfying the inequality: $1\leq m\leq n$,
which comprises reacting an organic compound represented by the formula (6):

$$R—L_n \quad (6)$$

wherein R is the same as defined above, L represents a leaving group and n represents an integer of no less than 1 (typically, n represents 1, 2, or 3) will be illustrated below.

Examples of the saturated hydrocarbon group represented by R include a straight chain or branched chain C1-20 alkyl group such as a methyl, ethyl, n-propyl, isopropyl, n-butyl, isobutyl, sec-butyl, n-pentyl, hexyl, heptyl, octyl, nonyl, n-decyl, undecyl, dodecyl, tridecyl, tetradecyl, pentadecyl, hexadecyl, heptadecyl, octadecyl, nonadecyl and icosyl group.

As the substituent of the substituted saturated hydrocarbon group, the substituents described below are exemplified;
for example, C5-20 aryl groups (for example, a 2-pyridyl, phenyl, 1-naphthyl and 2-naphthyl group), and C5-20 aryl groups substituted with at least one selected from an alkyl group (for example, a C1-3 alkyl group), an alkoxy group (for example, a C1-3 alkoxy group), an alkoxyalkyl group (for example, a C1-3 alkyl group substituted with a C1-3 alkoxy) and a fluorine atom (specifically, a 4-methylphenyl, 4-methoxyphenyl, 3-phenoxyphenyl, 2,3,5,6-tetrafluorophenyl, 2,3,5,6-tetrafluoro-4-methylphenyl, 2,3,5,6-tetrafluoro-4-methoxyphenyl and 2,3,5,6-tetrafluoro-4-methoxymethylphenyl group), C1-20 alkoxy groups and fluorine-substituted C1-20 alkoxy groups (for example, a methoxy, ethoxy, n-propoxy, isopropoxy, n-butoxy, isobutoxy, sec-butoxy, tert-butoxy and trifluoromethoxy group), C6-20 aryloxy groups (for example, a phenoxy group), and C6-20 aryloxy groups substituted with an alkyl group (for example, a C1-3 alkyl group) and/or an alkoxy group (for example, a C1-3 alkoxy group) (for example, a 2-methylphenoxy, 4-methylphenoxy, 4-methoxyphenoxy and 3-phenoxyphenoxy group), C7-20 aralkyloxy groups and C7-20 aralkyloxy groups substituted with at least one selected from an alkyl group (for example, a C1-3 alkyl group), an alkoxy group (for example, a C1-3 alkoxy group), an alkoxyalkyl group (for example, a C1-3 alkyl group substituted with a C1-3 alkoxy), a phenoxy group and a fluorine atom (for example, a benzyloxy, 4-methylbenzyloxy, 4-methoxybenzyloxy, 3-phenoxybenzyloxy group, 2,3,5,6-tetrafluorobenzyloxy, 2,3,5,6-tetrafluoro-4-methylbenzyloxy, 2,3,5,6-tetrafluoro-4-methoxybenzyloxy and 2,3,5,6-tetrafluoro-4-methoxymethylbenzyloxy group), a fluorine atom, C2-20 alkylcarbonyl groups (for example, an acetyl and ethylcarbonyl group), C7-20 arylcarbonyl groups (for example, a benzoyl group) and C7-20 arylcarbonyl groups substituted with an alkyl group (for example, a C1-3 alkyl group) and/or an alkoxy group (for example, a C1-3 alkoxy group) (for example, a benzoyl, 2-methylbenzoyl, 4-methylbenzoyl and 4-methoxybenzoyl group), and C8-20 aralkylcarbonyl groups (for example, a benzylcarbonyl group) and C8-20 aralkylcarbonyl groups substituted with an alkyl group (for example, a C1-3 alkyl group) and/or an alkoxy group (for example, a C1-3 alkoxy group) (for example, 4-methylbenzylcarbonyl and 4-methoxybenzylcarbonyl group), and a carboxyl group.

Specific examples of the substituted saturated hydrocarbon group include a fluoromethyl, trifluoromethyl, methoxymethyl, ethoxymethyl, methoxyethyl, tolyl, 4-methoxytolyl, 3-phenoxytolyl, 2,3,5,6-tetrafluorotolyl, 2,3,5,6-tetrafluoroparaxylyl, 2,3,5,6-tetrafluoro-4-methoxytolyl, 2,3,5,6-tetrafluoro-4-methoxymethyltolyl, 2-propylnaphthyl, methyl isobutyl ketone, phenacyl, 4-methylphenacyl and phenylacetyl. The saturated hydrocarbon group of the substituted or unsubstituted saturated hydrocarbon group is preferably a primary or secondary saturated hydrocarbon group, more preferably the primary saturated hydrocarbon group.

As the aromatic group represented by R, hydrocarbon type aromatic groups such as a phenyl and naphthyl group and heteroaromatic groups such as a pyridine and quinoline are exemplified.

Examples of the substituents of the substituted aromatic group include a sulfonamide group, a cyano group and an amide group in addition to those exemplified as the substituents of the above-mentioned A to I or the above-mentioned substituted saturated hydrocarbon group.

Among these substituents, the neighboring substituents may be bonded to form a ring together with the carbon atoms to which they are bonded. Among the substituents which may be substituted-on these aromatic groups, electron-withdrawing substituents are preferable in terms of reactivity. Examples of the electron-withdrawing substituents include a fluorine atom, an optionally substituted alkylcarbonyl group, an optionally substituted aralkylcarbonyl group, an optionally substituted arylcarbonyl group, a carboxyl group, a sulfonamide group and a cyano group.

Examples of the substituted aromatic compounds include cyanobenzene, terephthalonitrile, isophthalonitrile, orthophthalonitrile, fluorobenzene, 1,4-difluorobenzene, benzenesulfonamide, biphenyl, 2-phenylnaphthalene, diphenyl ether, 3-methylpyridine, 4-phenylpyridine, benzophenone and 1,2-diphenylethanone.

Examples of L include a chlorine atom, a bromine atom, an iodine atom, a nitro group, a sulfo group, an optionally substituted alkylsulfonyloxy group, an optionally substituted arylsulfonyloxy group, an optionally substituted alkylcarbonyloxy group or an optionally substituted arylcarbonyloxy group. In the case of having two or more substituents, these may be same or different.

Examples of the optionally substituted alkylsulfonyloxy group include a methanesulfonyloxy, ethanesulfonyloxy and trifluoromethanesulfonyloxy group.

Examples of the optionally substituted arylsulfonyloxy group include a paratoluenesulfonyloxy, benzenesulfonyloxy and 1-naphthalenesulfonyloxy group.

Examples of the optionally substituted alkylcarbonyloxy group include a trifluoroacetoxy and pentafluoroethylcarbonyloxy group.

Examples of the optionally substituted arylcarbonyloxy group include a tetrafluorobenzoyloxy and benzoyloxy group.

Examples of the compound of the formula (6) include 1-chlorobutane, 1-bromobutane, 1-iodobutane, 1-chloropentane, 1-bromopentane, 1-chloro-4-bromobutane, 1-chlorohexane, 1-bromohexane, 1,6-dibromohexane, 1-chloroheptane, 1-bromoheptane, 2-chloroheptane, 2-bromoheptane, 1-chlorooctane, 1-bromooctane, 2-chlorooctane, 2-bromooctane, benzyl chloride, benzyl bromide, 4-methoxybenzyl chloride, 4-methylbenzyl bromide, 3,4,5-trifluorobenzyl bromide, n-butyl paratoluenesulfonate, n-butyl methanesulfonate, n-pentyl paratoluenesulfonate, n-pentyl methanesulfonate, n-hexyl paratoluenesulfonate, n-hexyl methanesulfonate, n-heptyl paratoluenesulfonate, n-heptyl methanesulfonate, n-octyl paratoluenesulfonate, n-octyl methanesulfonate, n-butyl trifluoroacetate, n-butyl tetrafluorobenzoate, n-octyl trifluoroacetate, 4-chloronitrobenzene, 4-bromonitrobenzene, 2-chloronitrobenzene, 2-bromonitrobenzene, 4-cyanochlorobenzene, 4-cyanobromobenzene, 1-chloro-2,4-dinitrobenzene, tetrachloroterephthalonitrile, tetrachloroisophthalonitrile, tetrachloroorthophthalonitrile, 1,3-dichloro-4,6-dinitrobenzene, 2-chloroquinoline, 2-chloro-5-nitropyridine and 2-chloro-5-trifluoromethylpyridine.

When the organic compound having two or more substituent Ls is used, those may be different substituents and the reactivity below is usually shown; only the highest reactive substituent is sometimes substituted with a fluorine atom and same or defferent two or more substituents are sometimes substituted with fluorine atoms.

When the optionally substituted aromatic group represented by R is the hydrocarbon type aromatic group, the substituent, which has an electron-withdrawing group on para- or ortho-position and is subjected to the nucleophilic substitution fluorination reaction, is usually preferentially substituted with a fluorine atom. For example, in the reaction of 4-chloronitrobenzene, although the chlorine atom and the nitro group are both substituents which are subjected to the nucleophilic substitution fluorination reaction, the chlorine atom which has higher electron-withdrawing nitro group on para-position is preferentially substituted with a fluorine atom and 4-fluoronitrobenzene is usually selectively produced. Off course, the nitro group can be also substituted with a fluorine atom by selecting accordingly a reaction conditions such as use of a large excess of the fluorinating agent (1) and paradifluorobenzene can be also obtained.

When R is the optionally substituted heteroaromatic compound, the substituent on the 2-position, 4-position or 6-position for the hetero atom constituting the heteroaromatic ring, which is subjected to the nucleophilic fluorination reaction, is usually preferentially substituted with a fluorine atom. For example, in the case of 2-chloro-3-nitropyridine, the chlorine atom on 2-position is usually substituted to yield 2-fluoro-3-nitropyridine. Off course, the nitro group can be also substituted with a fluorine atom by selecting accordingly a reaction conditions such as use of a large excess of the fluorinating agent (1) and 2,3-difluoropyridine can be also obtained.

The amount of the fluorinating agent (1) to be used is usually 1 mole or more based on a fluoride ion relative to 1 mole of the substituent desired to substitute with a fluorine atom in the compound of the formula (6). There is no upper limit particularly and when the compound has only one substituent which is subjected to the nucleophilic substitution fluorination reaction, it is preferably in a range of about 1.5 to 5.0 moles from the viewpoint of the reaction efficiency. When the compound has two or more substituents which are subjected to the nucleophilic substitution fluorination reaction, the amount thereof may be accordingly set in a range wherein the substituent, which is not desired to subject to the fluorination reaction, is not substituted a fluorine atom based on the above-mentioned priority of the reactivity.

The present invention can be usually carried out in the presence of an organic solvent, water or a mixture thereof and can be also carried out in the absence of the solvent.

Examples of the organic solvents in the case of being carried out using the solvent include ether solvents such as methyl tert-butyl ether and tetrahydrofuran; nitrile solvents such as acetonitrile and propionitrile; aromatic hydrocarbon solvents such as toluene and xylene; aliphatic hydrocarbon solvents such as cyclohexane and n-heptane; amide solvents such as dimethylformamide and dimethylacetamide; and sulfur-containing solvents such as sulfolane and dimethylsulfoxide.

In the case of using the solvent, the amount thereof is not particularly limited and in consideration of volumetric efficiency, it is practically about 100 parts by weight or less relative to 1 part by weight of the fluorinating agent (1).

When the reaction temperature is too low, the reaction hardly proceeds and, when the reaction temperature is too high, side reaction such as degradation of the starting material or product may proceed. Therefore, the practical reaction temperature is usually a range of about −20 to 200° C.

The mixing order of the reaction agents is not particularly limited. For example, the fluorinating agent (1) may be added to the organic compound subjected to the nucleophilic substitution fluorination reaction under the reaction temperature condition and the reaction may be carried out in the reverse order. The reaction temperature may be adjusted after mixing both agents simultaneously.

The present reaction may be carried out under an atmospheric condition and a pressurized condition. The progress of the reaction can be confirmed by a conventional analytical means such as gas chromatography, high performance liquid chromatography, thin layer chromatography, NMR and IR.

After completion of the reaction, the fluorine-containing compound which is the reaction product can be isolated by conducting crystallization treatment, distillation or concentration of the organic layer obtained by extracting, if necessary by adding water and/or a water-insoluble solvent thereto. The fluorine-containing compound isolated may be further purified by a means such as distillation or column chromatography.

Herein, examples of the water-insoluble solvents include aromatic hydrocarbon solvents such as toluene, xylene and chlorobenzene; aliphatic hydrocarbon solvents such as pentane, hexane and heptane; halogenated hydrocarbon solvents such as dichloromethane, dichloroethane and chloroform; ether solvents such as diethyl ether, methyl tert-butyl ether and tetrahydrofuran; and ester solvents such as ethyl acetate.

Examples of the fluoride compounds thus obtained include 1-fluorobutane, 1-fluoropentane, 1,4-difluorobutane, 1-chloro-4-fluorobutane, 1-fluorohexane, 1,6-difluorohexane, 1-fluoroheptane, 2-fluoroheptane, 1-fluorooctane, 2-fluorooctane, benzyl fluoride, 4-methoxybenzyl fluoride, 4-methylbenzyl fluoride, 3,4,5-trifluorobenzyl fluoride, 4-fluoronitrobenzene, 2-fluoronitrobenzene, 4-cyanofluorobenzene, 1-fluoro-2,4-dinitrobenzene, tetrafluoroterephthalonitrile, tetrafluoroisophthalonitrile, tetrafluoroorthophthalonitrile, 1,3-difluoro-4,6-dinitrobenzene, 2-fluoroquinoline, 2-fluoro-5-nitropyridine and 2-fluoro-5-trifluoromethylpyridine.

After the reaction, the alkyl-substituted imidazolium cation can be recovered as the mixed alkyl-substituted imidazolium salt containing the substituent subjected to the nucleophilic substitution fluorination reaction. The mixed alkyl-substituted imidazolium salt recovered by filtration treatment or separation treatment from the reaction liquid, can be reused as the fluorinating agent (1) by exchanging the ion to fluoride ion again.

EXAMPLES

The present invention will be further illustrated in more detail by Examples. The present invention is not limited to these Examples.

Example 1

Example of Synthesis of the Fluorinating Agent (1) (x=1)

Into an Erlenmeyer flask, 22 g of 1-methyl-3-(n-butyl)imidazolium chloride and 200 g of water were charged and dissolved. After 16.1 g of silver(I) fluoride and 120 g of water were charged into another Erlenmeyer flask and dissolved, two aqueous solutions were mixed at 25° C. and the stirring was continued for 30 minutes at the same temperature. The crystalline precipitated after the reaction was filtered and washed with water. The filtrate and wash liquid obtained were joined and concentrated to obtain 24.5 g of 1-methyl-3-(n-butyl)imidazolium fluoride dihydrate. Yield: 100%.

Elementary analytical value: C: 49.5, H: 9.9, N: 14.5, F: 9.2.

Calculated value: C: 49.5, H: 9.9, N: 14.4, F: 9.8.

1H-NMR (δ ppm, DMSO-d6, TMS standard): 0.90 (t, 3H), 1.25 (m, 2H), 1.72 (m, 2H), 3.88 (s, 3H), 4.19 (t, 2H), 7.79 (d, 2H), 10.1 (bs, 1H)

Example 2

Example of Synthesis of the Fluorinating Agent (1) (x=1)

Into an Erlenmeyer flask, 5 g of 1-methyl-3-(n-hexyl)imidazolium chloride and 50 g of water were charged and dissolved. After 3.1 g of silver(I) fluoride and 50 g of water were charged into another Erlenmeyer flask and dissolved, two aqueous solutions were mixed at 25° C. and the stirring was continued for 30 minutes at the same temperature. The crystalline precipitated after the reaction was filtered and washed with water. The filtrate and wash liquid obtained were joined and concentrated to obtain 5.4 g of the colorless oil. The obtained oil was identified as 1-methyl-3-(n-hexyl)imidazolium fluoride dihydrate from the result of the elementary analysis.

Yield: 99%.

Elementary analytical value: C: 54.4, H: 11.0, N: 12.7, F: 8.3.

Calculated value: C: 54.0, H: 10.4, N: 12.6, F: 8.5.

1H-NMR (δ ppm, DMSO-d6, TMS standard): 0.90 (m, 3H), 1.29 (m, 6H), 1.78 (m, 2H), 3.89 (s, 3H), 4.18 (q, 2H), 7.82 (d, 2H), 10 (bs, 1H)

Example 3

Example of Synthesis of the Fluorinating Agent (1) (x=1)

Into an Erlenmeyer flask, 5.0 g of 1-methyl-3-(n-octyl)imidazolium chloride and 50 g of water were charged and dissolved. After 2.74 g of silver(I) fluoride and 50 g of water were charged into another Erlenmeyer flask and dissolved, two aqueous solutions were mixed at 25° C. and the stirring was continued for 30 minutes at the same temperature. The crystalline precipitated after the reaction was filtered and washed with water. The filtrate and wash liquid obtained were joined and concentrated to obtain 5.8 g of the colorless oil. The obtained oil was identified as 1-methyl-3-(n-octyl)imidazolium fluoride trihydrate from the result of the elementary analysis.

Yield: 100%.

Elementary analytical value: C: 53.6, H: 10.8, N: 10.1, F: 6.7.

Calculated value: C: 53.6, H: 11.0, N: 10.4, F: 7.1.

1H-NMR (δ ppm, DMSO-d6, TMS standard): 0.86 (m, 3H), 1.20 (m, 10H), 1.77 (m, 2H), 3.89 (s, 3H), 4.16 (q, 2H), 7.80 (d, 2H), 10 (bs, 1H)

Example 4

Example of Synthesis of the Fluorinating Agent (1) (x=0.475)

Into an Erlenmeyer flask, 5.0 g of 1-methyl-3-(n-butyl) imidazolium chloride and 50 g of water were charged and dissolved. After 1.72 g of silver(I) fluoride and 30 g of water were charged into another Erlenmeyer flask and dissolved, two aqueous solutions were mixed at 25° C. and the stirring was continued for 30 minutes at the same temperature. The crystalline precipitated after the reaction was filtered and washed with water. The filtrate and wash liquid obtained were joined and concentrated to obtain 5.8 g of the colorless oil. This oil was liquid even at 0° C. The obtained oil was identified as the dihydrate of the salt consisting of the mixed anion consisting of 47.5 mol % of the fluoride ion and 52.5 mol % of the chloride ion, and the 1-methyl-3-n-butylimidazolium cation from the result of elementary analysis.

Yield: 100%.
Elementary analytical value: C: 48.2, H: 9.5, N: 14.1, F: 4.6, Cl: 9.5.
Calculated value: C: 47.4, H: 9.5, N: 13.8, F: 4.5, Cl: 9.2.
1H-NMR (δ ppm, DMSO-d6, TMS standard): 0.88 (t, 3H), 1.25 (m, 2H), 1.78 (m, 2H), 3.90 (s, 3H), 4.19 (t, 2H), 7.85 (d, 2H), 10.0 (bs, 1H)

Example 5

Example of Synthesis of the Fluorinating Agent (1) (x=0.83)

Into an Erlenmeyer flask, 5.0 g of 1-methyl-3-(n-butyl) imidazolium chloride and 50 g of water were charged and dissolved. After 3.0 g of silver(I) fluoride and 30 g of water were charged into another Erlenmeyer flask and dissolved, two aqueous solutions were mixed at 25° C. and the stirring was continued for 30 minutes at the same temperature. The crystalline precipitated after the reaction was filtered and washed with water. The filtrate and wash liquid obtained were joined and concentrated to obtain 5.6 g of the colorless oil. A part of this oil crystallized at room temperature. The obtained oil was identified as the dihydrate of the salt consisting of the mixed anion consisting of 83 mol % of the fluoride ion and 17 mol % of the chloride ion, and the 1-methyl-3-n-butylimidazolium cation from the result of elementary analysis.

Yield: 99%.
Elementary analytical value: C: 47.3, H: 9.8, N: 13.8, F: 8.1, Cl: 3.1.
Calculated value: C: 48.7, H: 9.7, N: 14.2, F: 8.0, Cl: 3.1.
1H-NMR (δ ppm, DMSO-d6, TMS standard): 0.88 (t, 3H), 1.20 (m, 2H), 1.75 (m, 2H), 3.88 (s, 3H), 4.19 (t, 2H), 7.85 (d, 2H), 9.85 (s, 1H)

Example 6

Example of Synthesis of the Fluorinating Agent (1) (x=0.61)

Into an Erlenmeyer flask, 12.0 g of 1-methyl-3-(methoxyethoxymethyl)imidazolium chloride and 50 g of water were charged and dissolved. After 5.33 g of silver(I) fluoride and 30 g of water were charged into another Erlenmeyer flask and dissolved, two aqueous solutions were mixed at 25° C. and the stirring was continued for 30 minutes at the same temperature. The crystalline precipitated after the reaction was filtered and washed with water. The filtrate and wash liquid obtained were joined and concentrated to obtain 12.6 g of the colorless oil. A part of this oil crystallized at room temperature. The obtained oil was identified as the 1.3 hydrate of the salt consisting of the mixed anion consisting of 61 mol % of the fluoride ion and 39 mol % of the chloride ion, and the 1-methyl-3-(methoxyethoxymethyl)imidazolium cation from the result of elementary analysis.

Yield: 99%.
Elementary analytical value: C: 42.7, H: 8.0, N: 12.6, F: 5.8, Cl: 6.9.
Calculated value: C: 43.6, H: 8.0, N: 12.7, F: 5.3, Cl: 6.3.
1H-NMR (δ ppm, DMSO-d6, TMS standard): 3.19 (s, 3H), 3.44 (m, 2H), 3.67 (m, 2H), 3.97 (s, 3H), 5.69 (s, 2H), 7.95 (d, 2H), 10.1 (bs, 1H)

Example 7

Example of Synthesis of the Fluorinating Agent (1) (x=0.61)

Into an Erlenmeyer flask, 1.75 g of 1-methyl-3-(n-butyl) imidazolium chloride and 10 g of methanol (percentage of water content 1% by weight) were charged and dissolved. After 460 mg of potassium fluoride and 10 g of methanol (moisture content 1% by weight) were charged into another Erlenmeyer flask and dissolved, two methanol solutions were mixed at 25° C. and the stirring was continued for 30 minutes at the same temperature. The crystalline precipitated after the reaction was filtered and washed with methanol (percentage of water content 1% by weight). The filtrate and wash liquid obtained were joined and concentrated. A white powder precipitated from the concentrated oil was removed by decantation and then the white powder was washed with a small amount of methanol. The filtrate, the washed liquid and the concentrated oil were joined and concentrated again to obtain 2.10 g of the colorless oil. This oil crystallized by leaving at room temperature. The obtained oil was identified as the salt consisting of the mixed anion consisting of 61 mol % of the fluoride ion and 39 mol % of the chloride ion, and the 1-methyl-3-(n-butyl)imidazolium cation containing ⅔ mole of methanol and ⅘ mole of water from the result of elementary analysis.

Yield based on the imidazolium cation: 100%.
Elementary analytical value: C: 48.5, H: 10.3, N: 13.7, F: 5.7, Cl: 6.7.
Calculated value: C: 49.5, H: 9.8, N: 13.3, F: 5.5, Cl: 6.6.
1H-NMR (δ ppm, DMSO-d6, TMS standard): 0.90 (t, 3H), 1.23 (m, 2H), 1.78 (m, 2H), 3.10 (s, Me group of methanol), 3.90 (s, 3H), 4.22 (t, 2H), 7.85 (d, 2H), 8.5 (bs, 1H)

Example 8

Example of Synthesis of the Fluorinating Agent (1) (x=0.47)

Into an Erlenmeyer flask, 8.20 g of 1-methyl-3-(n-butyl) imidazolium chloride and 50 g of methanol (percentage of water content 1% by weight) were charged and dissolved. After 1.4 g of potassium fluoride and 35 g of methanol (percentage of water content 1% by weight) were charged into another Erlenmeyer flask and dissolved, two methanol solutions were mixed at 25° C. and the stirring was continued for 30 minutes at the same temperature. The crystalline precipitated after the reaction was filtered and washed with methanol (percentage of water content 1% by weight). The filtrate and wash liquid obtained were joined and concentrated. A white powder precipitated from the concentrated oil was removed by decantation and then the white powder was washed with a small amount of methanol. The filtrate, the washed liquid and the concentrated oil were joined and concentrated again to obtain 9.61 g of the colorless oil. This oil crystallized by leaving at room temperature. The obtained oil was identified as the salt consisting of the mixed anion consisting of 47 mol % of the fluoride ion and 53 mol % of the chloride ion, and the 1-methyl-3-(n-butyl)imidazolium cation containing ⅔ mole of methanol and 1 mole of water from the result of elementary analysis.

Yield based on the imidazolium cation: 100%.

Elementary analytical value: C: 49.5, H: 10.1, N: 14.0, F: 4.5, Cl: 9.6.

Calculated value: C: 50.4, H: 9.6, N: 13.6, F: 4.3, Cl: 9.1.

1H-NMR ($\delta$ ppm, DMSO-d6, TMS standard): 0.90 (t, 3H), 1.23 (m, 2H), 1.78 (m, 2H), 3.10 (s, Me group of methanol), 3.90 (s, 3H), 4.21 (t, 2H), 7.90 (d, 2H), 8.5 (bs, 1H)

(The Followings are the Fluorination Reactions Using the Fluorinating Agent (1))

Example 9

Into a 50 mL flask equipped with a reflux condenser, 500 mg of the fluorinating agent (1) synthesized in Example 1 and 171 mg of benzyl bromide were charged and the resulting mixture was stirred for 5 hours at 80° C. After cooling to room temperature, 5 g of ethyl acetate was added thereto and stirred. The mixture was separated to two layers by standing. The upper layer was analyzed by gas chromatography (internal standard method) to find that the main product was benzyl fluoride.

Yield: 95%.

Example 10

According to the same manner as that described in Example 9, the main product was 1-fluorooctane except that 284 mg of n-octyl paratoluenesulfonate was used in place of 171 mg of benzyl bromide used in Example 9 and the mixture was stirred for 3 hours at 150° C.

Yield: 98%.

Example 11

According to the same manner as that described in Example 9, the main product was 1-fluorooctane except that 193 mg of 1-bromooctane was used in place of 171 mg of benzyl bromide used in Example 9 and the mixture was stirred for 3 hours at 100° C.

Yield: 90%.

Example 12

According to the same manner as that described in Example 9, the main product was 4-fluoronitrobenzene except that 158 mg of 4-chloronitrobenzene was used in place of 171 mg of benzyl bromide used in Example 9 and the mixture was stirred for 3 hours at 150° C.

Yield: 88%.

Example 13

Into a 50 mL flask equipped with a reflux condenser, 640 mg of the fluorinating agent (1) synthesized in Example 4 and 254 mg of benzyl chloride were charged and the resulting mixture was stirred for 3 hours at 80° C. After cooling to room temperature, 5 g of ethyl acetate was added thereto and stirred. The mixture was separated to two layers by standing. The upper layer was analyzed by gas chromatography (internal standard method) to find that the main product was benzyl fluoride.

Yield: 75% (based on benzyl chloride). Benzyl chloride was recovered in 25%. Yield based on the fluoride ion of the fluorinating agent (1) was 100%.

Example 14

Into a 50 mL flask equipped with a reflux condenser, 300 mg of the fluorinating agent (1) synthesized in Example 5, 127 mg of benzyl chloride and 500 mg of acetonitrile were charged and the resulting mixture was stirred for 3 hours at 80° C. After cooling to room temperature, 5 g of ethyl acetate was added thereto and stirred. The mixture was separated to two layers by standing. The upper layer was analyzed by gas chromatography (internal standard method) to find that the main product was benzyl fluoride. Yield: 99% (based on benzyl chloride). Benzyl chloride was recovered in 1%. Yield based on the fluoride ion of the fluorinating agent (1) was 79%.

Example 15

Into a 50 mL flask equipped with a reflux condenser, 330 mg of the fluorinating agent (1) synthesized in Example 2 and 149 mg of 1-octyl chloride were charged and the resulting mixture was stirred for 4 hours at 100° C. After cooling to room temperature, 5 g of ethyl acetate and 5 g of water were added thereto and stirred. The mixture was separated to two layers by standing. The upper layer was analyzed by gas chromatography (internal standard method) to find that the main product was 1-octyl fluoride. Yield: 63% (based on 1-octyl chloride). 1-octyl chloride was recovered in 32%.

Example 16

According to the same manner as that described in Example 15, 1-octyl fluoride was obtained except that 320 mg of the fluorinating agent (1) synthesized in Example 3 was used in place of the fluorinating agent (1) synthesized in Example 2.

Yield: 64% (based on 1-octyl chloride). 1-octyl chloride was recovered in 32%.

Example 17

Into a 50 mL flask equipped with a reflux condenser, 500 mg of the fluorinating agent (1) synthesized in Example 1, 236 mg of 2,6-dibromopyridine and 2 g of acetonitrile were charged and the resulting mixture was stirred for 3 hours at 80° C. After cooling to room temperature, 5 g of ethyl acetate and 5 g of water were added thereto and stirred. The mixture was separated to two layers by standing. The upper layer was analyzed by gas chromatography (internal standard method) to find that the main product was 2-fluoro-6-bromopyridine.

Yield: 78% (based on 2,6-dibromopyridine). 2,6-dibromopyridine was recovered in 20%.

Example 18

Into a 50 mL flask equipped with a reflux condenser, 600 mg of the fluorinating agent (1) synthesized in Example 1 and 250 mg of benzyl chloride were charged and the resulting mixture was stirred for 3 hours at 80° C. After cooling to room temperature, 5 g of n-hexane and 5 g of water were added thereto and stirred. The mixture was separated to two layers by standing. The upper layer was analyzed by gas chromatography (internal standard method) to find that the main product was benzyl fluoride.

Yield: 94% (based on benzyl chloride). Benzyl chloride was recovered in 6%.

Example 19

Recycle Use of the Fluorinating Agent (1)

To the water layer obtained in Example 18, an aqueous solution obtained by dissolving 390 mg of silver fluoride with 5 g of water was added and the resulting mixture was stirred for 2 hours at 25° C. The crystalline precipitated was removed by filtration and the mixture was concentrated to obtain 605 mg of the pale yellow oil. To this oil, 250 mg of benzyl chloride was added and the mixture was stirred for 3 hours at 80° C. After cooling to room temperature, 5 g of n-hexane and 5 g of water were added thereto and stirred. The mixture was separated to two layers by standing. The upper layer was analyzed by gas chromatography (internal standard method) to find that the main product was benzyl fluoride.

Yield: 95% (based on benzyl chloride). Benzyl chloride was recovered in 5%.

Example 20

Into a 50 mL flask equipped with a reflux condenser, 430 mg of 1-methyl-3-(n-butyl)imidazolium fluoride obtained in Example 7 and 127 mg of benzyl chloride were charged and the resulting mixture was stirred for 3 hours at 80° C. After cooling to room temperature, 5 g of ethyl acetate was added thereto and stirred. The mixture was separated to two layers by standing. The upper layer was analyzed by gas chromatography (internal standard method) to find that the main product was benzyl fluoride. Yield: 95%.

Example 21

Into an Erlenmeyer flask, 5.0 g of 1-methyl-3-(n-butyl) imidazolium chloride and 50 g of methanol (percentage of water content 1% by weight) were charged and dissolved. After 1.33 g of potassium fluoride and 33 g of methanol (percentage of water content 1% by weight) were charged into another Erlenmeyer flask and dissolved, two methanol solutions were mixed at 25° C. and the stirring was continued for 30 minutes at the same temperature. The crystalline precipitated after the reaction was filtered and washed with methanol (percentage of water content 1% by weight). The filtrate and wash liquid obtained were joined and concentrated. A white powder precipitated from the concentrated oil was removed by decantation and then the white powder was washed with a small amount of methanol. The filtrate, the washed liquid and the concentrated oil were joined and concentrated again to obtain 4.76 g of the colorless oil.

Into a 50 mL flask equipped with a reflux condenser, 400 mg of the colorless oil synthesized (the fluorinating agent (1)) and 284 mg of n-octyl p-toluenesulfonate were charged and the resulting mixture was stirred for 5 hours at 80° C. After cooling to room temperature, 5 g of ethyl acetate was added thereto and stirred. The mixture was separated to two layers by standing. The upper layer was analyzed by gas chromatography (internal standard method) to find that the main product was n-octyl fluoride.

Yield: 98%.

INDUSTRIAL APPLICABILITY

According to the present invention, an aliphatic and aromatic fluorine-containing compound can be efficiently and readily manufactured without using a highly corrosive and toxic hydrogen fluoride or the salt thereof. Further, since the fluorinating agent of the present invention has also the nature of an ionic liquid in itself, it is easy to recover and reuse thereof. Since the fluorinating agent whose melting point is below room temperature can be obtained by selecting x in the formula (1) accordingly, the reaction using it can be carried out under the wide temperature condition. Therefore, it is also advantageous in the point of handling industrially and environment.

The invention claimed is:

1. A method for producing a fluorine-containing organic compound represented by the formula (7):

wherein R represents a substituted or unsubstituted saturated hydrocarbon group, or a substituted or unsubstituted aromatic group and m represents an integer satisfying the inequality: $1 \leq m \leq n$, which comprises reacting a fluorinating agent represented by the formula (1):

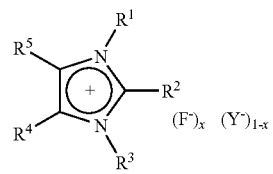

wherein $R^1$ and $R^3$ are the same or different, and represent an optionally substituted alkyl group, $R^2$, $R^4$ and $R^5$ are the same or different, and represent a hydrogen atom or an optionally substituted alkyl group, x satisfies 0<x<1, and $Y^-$ represents a monovalent anion other than a fluoride ion, with an organic compound of the formula (6):

wherein R is the same as defined above, L represents a leaving group and n represents an integer of 1, 2 or 3.

2. The method according to claim 1, wherein R is the optionally substituted saturated hydrocarbon group.

3. The method according to claim 1, wherein R is the optionally substituted aromatic group.

4. The method according to claim 1, wherein L is a chlorine atom, a bromine atom, an iodine atom, a nitro group, a sulfo group, an optionally substituted alkylsulfonyloxy group, an optionally substituted arylsulfonyloxy group, an optionally substituted alkylcarbonyloxy group or an optionally substituted arylcarbonyloxy group.

5. The method according to claim 1, wherein the fluorinating agent of the formula (1) is an anhydrous salt.

6. The method according to claim 1, wherein the fluorinating agent is an adduct of methanol, water or both.

7. The method according to claim 1, wherein X is 1.

8. The method according to claim 1, wherein X satisfies 0<X<1.

9. The method according to claim 8, wherein X satisfies 0.4<X<0.9.

10. The method according to claim 1, wherein the monovalent anion represented by $Y^-$ is a halide ion, a borate ion, a phosphate ion, an antimonate ion, a sulfonate ion, a nitrate ion, a carbonate ion, a carboxylate ion or an amide ion.

11. The method according to claim 10, wherein $Y^-$ is $Cl^-$ or $Br^-$.

* * * * *